United States Patent
Arnold et al.

(10) Patent No.: US 6,524,837 B1
(45) Date of Patent: Feb. 25, 2003

(54) HYDANTOINASE VARIANTS WITH IMPROVED PROPERTIES AND THEIR USE FOR THE PRODUCTION OF AMINO ACIDS

(75) Inventors: Frances H. Arnold, Pasadena, CA (US); Oliver May, Stuttgart (DE); Karlheinz Drauz, Freigericht (DE); Andreas Bommarius, Frankfurt/M (DE)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/497,585

(22) Filed: Feb. 3, 2000

Related U.S. Application Data

(60) Provisional application No. 60/157,427, filed on Oct. 4, 1999, and provisional application No. 60/126,923, filed on Mar. 29, 1999.

(51) Int. Cl.[7] .................................................. C12N 9/86
(52) U.S. Cl. ........................................................ 435/231
(58) Field of Search ......................................... 435/231

(56) References Cited

U.S. PATENT DOCUMENTS

| | | | |
|---|---|---|---|
| 3,964,970 A | 6/1976 | Dinelli et al. ................... | 195/2 |
| 4,065,353 A | 12/1977 | Cecere et al. ................... | 195/2 |
| 4,094,741 A | 6/1978 | Yamada et al. ................. | 195/29 |
| 4,111,749 A | 9/1978 | Degen et al. .................... | 195/2 |
| 4,816,393 A | 3/1989 | Siedel et al. .................... | 435/18 |
| 5,516,660 A | 5/1996 | Wagner et al. ................ | 435/106 |
| 5,608,076 A | 3/1997 | Kottenhahn et al. ..... | 548/317.1 |
| 5,679,571 A | * 10/1997 | Burtscher et al. ........... | 435/325 |
| 5,714,355 A | 2/1998 | Wagner et al. ................ | 435/106 |
| 5,807,710 A | 9/1998 | Galli et al. ................. | 435/69.1 |
| 5,827,717 A | 10/1998 | Wagner et al. ............... | 435/195 |
| 5,834,258 A | 11/1998 | Grifantini et al. ........... | 435/106 |
| 5,877,003 A | 3/1999 | Grifantini et al. .......... | 435/228 |

OTHER PUBLICATIONS

GenBank Accession No. AAc09759 (1998).*
Mukohara et al. A thermostable hydantoinase of *Bacillus stearothermophilus* NS1122A: cloning, sequencing, and high expression of the enzyme gene, and some properties of the expressed enzyme. Biosci Biotechnol Biochem Sep 1994;58(9):1621–6.*
GenBank Accession No. Q45515 (Jul. 15, 1998).*
LaPointe et al. Cloning, sequencing, and expression in *Escherichia coli* of the D–hydantoinase gene from *Pseudomonas putida* and distribution of homologous genes in other microorganisms. Appl Environ Microbiol Mar. 1994;60(3):888–95.*
GenBank Accession No. Q59699 (Jul. 15, 1998).*
Matsuda et al. Molecular cloning and sequencing of a cDNA encoding dihydropyrimidinase from the rat liver. Biochim Biophys Acta Jun. 7, 1996;1307(2):140–4.*
GenBank Accession No. Q63150 (Jul. 15, 1998).*
GenBank Accession No. JC5315 (May 1, 1997).*
May et al. Substrate–dependent enantioselectivity of a novel hydantoinase from Arthrobacter aurescens DSM 3745: purification and characterization as new member of cyclic amidase. J Biotechnol Mar. 26, 1998;61(1):1–13.*
GenBank Accession No. P81006 (Jul. 15, 1998).*
GenBank Accession No. CAA18902 (May 8, 1998).*
GenBank Accession No. Q44184 (Jul. 15, 1998).*
O. May (1998) "The Hydantoinase from *Arthrobacter aurescens* DSM 3745 and its Relation to other Hydantoinase," Dissertation.
C. Syldatk et al. (1992) "Microbial and Enzymatic Production of D–Amino Acids from DL–5–Monosubstituted Hydantoins," In: Biocatalytic Production of Amino Acids and Derivatives (Rozzell, J.D. & Wagner, F. eds.) Hanser Publishers, NY.
R. Grifantini et al. (1998) Efficient conversion of 5–substituted hydantoins to D–χ–amino acids using recombinant *Escherichia coli* strains, Microbiology, 144, 947–954.
T. Wagner et al. (1996) Production of L–methionine from D,L–5–(2–methylthioethyl)hydantoin by resting cells of a new mutant strain of Arthrobacter species DSM 7330, Journal of Biotechnology, 46, 63–68.

* cited by examiner

*Primary Examiner*—Ponnathapuachuta Murthy
*Assistant Examiner*—Kathleen Kerr
(74) *Attorney, Agent, or Firm*—Shapiro & Dupont LLP

(57) ABSTRACT

Hydantoinase enzymes which are mutants of a previously isolated hydantoinase having the amino acid SEQ. ID. NO. 2. The mutants include amino acid substitutions at positions 95, 154, 180, 251 and/or 255 of the wild type hydantoinase (SEQ. ID. NO. 2). The mutant hydantoinases, like the parent hydantoinase, are used in the production of optically pure amino acids.

9 Claims, 4 Drawing Sheets

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
  (A) LENGTH: 1377 nucleotides
  (B) TYPE: nucleotide
  (C) STRANDEDNESS: single
  (D) TOPOLOGY: linear (ii) MOLECULE TYPE: nucleic acid (xi) SEQUENCE DESCRIPTION: SEQ ID NO: 1

```
ATGTTTGACG TAATAGTTAA GAACTGCCGT ATGGTGTCCA GCGACGGAAT CACCGAGGCA      60

GACATTCTGG TGAAAGACGG CAAAGTCGCC GCAATCAGCT CGGACACAAG TGATGTTGAG     120

GCGAGCCGAA CCATTGACGC GGGTGGCAAG TTCGTGATGC CGGGCGTGGT CGATGAACAT     180

GCGAGCCGAA CCATTGACGC GGGTGGCAAG TTCGTGATGC CGGGCGTGGT CGATGAACAT     240

TCTGCGGCCG TGGGAGGCAT CACCACCATC ATCGAGATGC CGATAACCTT CCCGCCCACC     300

ACCACTTTGG ACGCCTTCCT CGAAAAGAAG AAGCAGGCGG GGCAGCGGTT GAAAGTTGAC     360

TTCGCGCTCT ATGGCGGTGG AGTGCCGGGA AACCTGCCCG AGATCCGCAA AATGCACGAC     420

GCCGGCGCAG TGGGCTTCAA GTCAATGATG GCAGCCTCAG TTCCGGGCAT GTTCGACGCC     480

GTCAGCGACG GCGAACTGTT CGAAATCTTC CAGGAGATCG CAGCCTGTGG TTCAGTCGTC     540

GTGGTCCATG CCGAGAATGA AACGATCATT CAAGCGCTCC AGAAGCAGAT CAAAGCCGCT     600

GGTCGCAAGG ACATGGCCGC CTACGAGGCA TCCCAACCAG TTTTCCAGGA GAACGAGGCC     660

ATTCAGCGTG CGTTACTACT GCAGAAAGAA GCCGGCTGTC GACTGATTGT GCTTCACGTG     720

AGCAACCCTG ACGGGGTCGA GCTGATACAT CAGGCGCAAT CCGAGGGCCA GGACGTCCAC     780

TGCGAGTCGG GTCCGCAGTA TCTGAATATC ACCACGGACG ACGCCGAACG AATCGGACCG     840

TATATGAAGG TCGCGCCGCC CGTCCGCTCA GCCGAGATGA ACGTCAGATT ATGGGAACAA     900

CTTGAGAACG GGCTCATCGA CACCCTTGGG TCAGACCACG GCGGACATCC TGTCGAGGAC     960

AAAGAACCCG GCTGGAAGGA CGTGTGGAAA GCCGGCAACG GTGCGCTGGG CCTTGAGACA    1020

TCCCTGCCTA TGATGCTGAC CAACGGAGTG AATAAAGGCA GGCTATCCTT GGAACGCCTC    1080

GTCGAGGTGA TGTGCGAGAA ACCTGCGAAG CTCTTTGGCA TCTATCCGCA GAAGGGCACG    1140
```

```
CTACAGGTTG GTTCCGACGC CGATCTGCTC ATCCTCGATC TGGATATTGA CACCAAAGTG    1200

GATGCCTCGC AGTTCCGATC CCTGCATAAG TACAGCCCGT TCGACGGGAT GCCCGTCACG    1260

GGTGCACCGG TTCTGACGAT GGTGCGCGGA ACGGTGGTGG CAGAGAAGGG AGAAGTTCTG    1320

GTCGAGCAGG GATTCGGCCA GTTCGTCACC CGTCACGACT ACGAGGCGTC GAAGTGA       1377
```

(2) INFORMATION FOR SEQ ID NO: 2:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 2

```
Met Phe Asp Val Ile Val Lys Asn Cys Arg Met Val Ser Ser Asp Gly
                  5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Ile Glu Met Pro Ile Thr
                 85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300
```

```
Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
            405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
450                 455                 458

(2) INFORMATION FOR SEQ ID NO: 3:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 3

ATGTTTGACG TAATAGTTAA GAACTGCCGT ATGGTGTCCA GCGACGGAAT CACCGAGGCA      60

GACATTCTGG TGAAAGACGG CAAAGTCGCC GCAATCAGCT CGGACACAAG TGATGTTGAG     120

GCGAGCCGAA CCATTGACGC GGGTGGCAAG TTCGTGATGC CGGGCGTGGT CGATGAACAT     180

GCGAGCCGAA CCATTGACGC GGGTGGCAAG TTCGTGATGC CGGGCGTGGT CGATGAACAT     240

TCTGCGGCCG TGGGAGGCAT CACCACCATC ATCGAGATGC CGATAACCTT CCCGCCCACC     300

ACCACTTTGG ACGCCTTCCT CGAAAAGAAG AAGCAGGCGG GGCAGCGGTT GAAAGTTGAC     360

TTCGCGCTCT ATGGCGGTGG AGTGCCGGGA AACCTGCCCG AGATCCGCAA AATGCACGAC     420

GCCGGCGCAG TGGGCTTCAA GTCAATGATG GCAGCCTCAG CTCCGGGCAT GTTCGACGCC     480

GTCAGCGACG GCGAACTGTT CGAAATCTTC CAGGAGATCG CAGCCTGTGG TTCAGTCGTC     540

GTGGTCCATG CCGAGAATGA AACGATCATT CAAGCGCTCC AGAAGCAGAT CAAAGCCGCT     600

GGTCGCAAGG ACATGGCCGC CTACGAGGCA TCCCAACCAG TTTTCCAGGA GAACGAGGCC     660

ATTCAGCGTG CGTTACTACT GCAGAAAGAA GCCGGCTGTC GACTGATTGT GCTTCACGTG     720

AGCAACCCTG ACGGGTCGA GCTGATACAT CAGGCGCAAT CCGAGGGCCA GGACGTCCAC     780

TGCGAGTCGG GTCCGCAGTA TCTGAATATC ACCACGGACG ACGCCGAACG AATCGGACCG     840

TATATGAAGG TCGCGCCGCC CGTCCGCTCA GCCGAGATGA ACGTCAGATT ATGGGAACAA     900

CTTGAGAACG GGCTCATCGA CACCCTTGGG TCAGACCACG GCGGACATCC TGTCGAGGAC     960

AAAGAACCCG GCTGGAAGGA CGTGTGGAAA GCCGGCAACG GTGCGCTGGG CCTTGAGACA    1020

TCCCTGCCTA TGATGCTGAC CAACGGAGTG AATAAAGGCA GGCTATCCTT GGAACGCCTC    1080
```

```
GTCGAGGTGA TGTGCGAGAA ACCTGCGAAG CTCTTTGGCA TCTATCCGCA GAAGGGCACG    1140

CTACAGGTTG GTTCCGACGC CGATCTGCTC ATCCTCGATC TGGATATTGA CACCAAAGTG    1200

GATGCCTCGC AGTTCCGATC CCTGCATAAG TACAGCCCGT TCGACGGGAT GCCCGTCACG    1260

GGTGCACCGG TTCTGACGAT GGTGCGCGGA ACGGTGGTGG CAGAGAAGGG AGAAGTTCTG    1320

GTCGAGCAGG GATTCGGCCA GTTCGTCACC CGTCACGACT ACGAGGCGTC GAAGTGA       1377
```

(2) INFORMATION FOR SEQ ID NO: 4:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 4

```
Met Phe Asp Val Ile Val Lys Asn Cys Arg Met Val Ser Ser Asp Gly
                 5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Ile Glu Met Pro Ile Thr
                 85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Ala Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
    290                 295                 300
```

```
Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
            325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455         458

(2) INFORMATION FOR SEQ ID NO: 5:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 5

ATGTTTGACG TAATAGTTAA GAACTGCCGT ATGGTGTCCA GCGACGGAAT CACCGAGGCA      60

GACATTCTGG TGAAAGACGG CAAAGTCGCC GCAATCAGCT CGGACACAAG TGATGTTGAG     120

GCGAGCCGAA CCATTGACGC GGGTGGCAAG TTCGTGATGC CGGGCGTGGT CGATGAACAT     180

GCGAGCCGAA CCATTGACGC GGGTGGCAAG TTCGTGATGC CGGGCGTGGT CGATGAACAT     240

TCTGCGGCCG TGGGAGGCAT CACCACCATC ATCGAGATGC CGTTAACCTT CCCGCCCACC     300

ACCACTTTGG ACGCCTTCCT CGAAAAGAAG AAGCAGGCGG GGCAGCGGTT GAAAGTTGAC     360

TTCGCGCTCT ATGGCGGTGG AGTGCCGGGA AACCTGCCCG AGATCCGCAA AATGCACGAC     420

GCCGGCGCAG TGGGCTTCAA GTCAATGATG GCAGCCTCAG TTCCGGGCAT GTTCGACGCC     480

GTCAGCGACG GCGAACTGTT CGAAATCTTC CAGGAGATCG CAGCCTGTGG TTCAGTCGTC     540

GTGGTCCATG CCGAGAATGA AACGATCATT CAAGCGCTCC AGAAGCAGAT CAAAGCCGCT     600

GGTCGCAAGG ACATGGCCGC CTACGAGGCA TCCCAACCAG TTTTCCAGGA GAACGAGGCC     660

ATTCAGCGTG CGTTACTACT GCAGAAAGAA GCCGGCTGTC GACTGATTGT GCTTCACGTG     720

AGCAACCCTG ACGGGGTCGA GCTGATACAT CAGGCGCAAT CCGAGGGCCA GGACGTCCAC     780

TGCGAGTCGG GTCCGCAGTA TCTGAATATC ACCACGGACG ACGCCGAACG AATCGGACCG     840

TATATGAAGG TCGCGCCGCC CGTCCGCTCA GCCGAGATGA ACGTCAGATT ATGGGAACAA     900

CTTGAGAACG GGCTCATCGA CACCCTTGGG TCAGACCACG GCGACATCC TGTCGAGGAC     960

AAAGAACCCG GCTGGAAGGA CGTGTGGAAA GCCGGCAACG GTGCGCTGGG CCTTGAGACA    1020

TCCCTGCCTA TGATGCTGAC CAACGGAGTG AATAAAGGCA GGCTATCCTT GGAACGCCTC    1080
```

```
GTCGAGGTGA TGTGCGAGAA ACCTGCGAAG CTCTTTGGCA TCTATCCGCA GAAGGGCACG    1140

CTACAGGTTG GTTCCGACGC CGATCTGCTC ATCCTCGATC TGGATATTGA CACCAAAGTG    1200

GATGCCTCGC AGTTCCGATC CCTGCATAAG TACAGCCCGT TCGACGGGAT GCCCGTCACG    1260

GGTGCACCGG TTCTGACGAT GGTGCGCGGA ACGGTGGTGG CAGAGAAGGG AGAAGTTCTG    1320

GTCGAGCAGG GATTCGGCCA GTTCGTCACC CGTCACGACT ACGAGGCGTC GAAGTGA       1377
```

(2) INFORMATION FOR SEQ ID NO: 6:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 6

```
Met Phe Asp Val Ile Val Lys Asn Cys Arg Met Val Ser Ser Asp Gly
                 5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Glu Met Pro Leu Thr
                 85                  90                  95

Phe Pro Pro Thr Thr Thr Leu Asp Ala Phe Leu Glu Lys Lys Gln
                100                 105                 110

Ala Gly Gln Arg Leu Lys Val Asp Phe Ala Leu Tyr Gly Gly Gly Val
            115                 120                 125

Pro Gly Asn Leu Pro Glu Ile Arg Lys Met His Asp Ala Gly Ala Val
        130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285

Arg Ser Ala Glu Met Asn Val Arg Leu Trp Glu Gln Leu Glu Asn Gly
```

```
                290                  295                  300
Leu Ile Asp Thr Leu Gly Ser Asp His Gly Gly His Pro Val Glu Asp
305                 310                  315                 320

Lys Glu Pro Gly Trp Lys Asp Val Trp Lys Ala Gly Asn Gly Ala Leu
                325                  330                 335

Gly Leu Glu Thr Ser Leu Pro Met Met Leu Thr Asn Gly Val Asn Lys
                340                  345                 350

Gly Arg Leu Ser Leu Glu Arg Leu Val Glu Val Met Cys Glu Lys Pro
                355                  360                 365

Ala Lys Leu Phe Glu Ile Tyr Pro Gln Lys Gly Thr Leu Gln Val Gly
            370                  375                 380

Ser Asp Ala Asp Leu Leu Ile Leu Asp Leu Asp Ile Asp Thr Lys Val
385                 390                  395                 400

Asp Ala Ser Gln Phe Arg Ser Leu His Lys Tyr Ser Pro Phe Asp Gly
                405                  410                 415

Met Pro Val Thr Gly Ala Pro Val Leu Thr Met Val Arg Gly Thr Val
                420                  425                 430

Val Ala Glu Lys Gly Glu Val Leu Val Glu Gln Gly Phe Gly Gln Phe
            435                  440                 445

Val Thr Arg His Asp Tyr Glu Ala Ser Lys
450                  455             458

(2) INFORMATION FOR SEQ ID NO: 7:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 7

ATGTTTGACG TAATAGTTAA GAACTGCCGT ATGGTGTCCA GCGACGGAAT CACCGAGGCA      60

GACATTCTGG TGAAAGACGG CAAAGTCGCC GCAATCAGCT CGGACACAAG TGATGTTGAG     120

GCGAGCCGAA CCATTGACGC GGGTGGCAAG TTCGTGATGC CGGGCGTGGT CGATGAACAT     180

GCGAGCCGAA CCATTGACGC GGGTGGCAAG TTCGTGATGC CGGGCGTGGT CGATGAACAT     240

TCTGCGGCCG TGGGAGGCAT CACCACCATC ATCGAGATGC CGATAACCTT CCCGCCCACC     300

ACCACTTTGG ACGCCTTCCT CGAAAAGAAG AAGCAGGCGG GCAGCGGTT GAAAGTTGAC      360

TTCGCGCTCT ATGGCGGTGG AGTGCCGGGA AACCTGCCCG AGATCCGCAA AATGCACGAC     420

GCCGGCGCAG TGGGCTTCAA GTCAATGATG GCAGCCTCAG TTCCGGGCAT GTTCGACGCC     480

GTCAGCGACG GCGAACTGTT CGAAATCTTC CAGGAGATCG CAGCCTGTGG TTCAGTCGTC     540

GTGGTCCATG CCGAGAATGA AACGATCATT CAAGCGCTCC AGAAGCAGAT CAAAGCCGCT     600

GGTCGCAAGG ACATGGCCGC CTACGAGGCA TCCCAACCAG TTTTCCAGGA GAACGAGGCC     660

ATTCAGCGTG CGTTACTACT GCAGAAAGAA GCCGGCTGTC GACTGATTGT GCTTCACGTG     720

AGCAACCCTG ACGGGGTCGA GCTGATACAT CAGGCGCAAT CCGAGGGCCA GGACGTCCAC     780

TGCGAGTCGG GTCCGCAGTA TCTGAATATC ACCACGGACG ACGCCGAACG AATCGGACCG     840

TATATGAAGG TCGCGCCGCC CGTCCGCTCA GCCGAGATGA ACGCCAGATT ATGGGAACAA     900

CTTGAGAACG GGCTCATCGA CACCCTTGGG TCAGACCACG GCGACATCC TGTCGAGGAC      960

AAAGAACCCG GCTGGAAGGA CGTGTGGAAA GCCGGCAACG GTGCGCTGGG CCTTGAGACA    1020
```

```
TCCCTGCCTA TGATGCTGAC CAACGGAGTG AATAAAGGCA GGCTATCCTT GGAACGCCTC      1080

GTCGAGGTGA TGTGCGAGAA ACCTGCGAAG CTCTTTGGCA TCTATCCGCA GAAGGGCACG      1140

CTACAGGTTG GTTCCGACGC CGATCTGCTC ATCCTCGATC TGGATATTGA CACCAAAGTG      1200

GATGCCTCGC AGTTCCGATC CCTGCATAAG TACAGCCCGT TCGACGGGAT GCCCGTCACG      1260

GGTGCACCGG TTCTGACGAT GGTGCGCGGA ACGGTGGTGG CAGAGAAGGG AGAAGTTCTG      1320

GTCGAGCAGG GATTCGGCCA GTTCGTCACC CGTCACGACT ACGAGGCGTC GAAGTGA         1377

(2) INFORMATION FOR SEQ ID NO: 8:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 8

Met Phe Asp Val Ile Val Lys Asn Cys Arg Met Val Ser Ser Asp Gly
              5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
65                  70                  75                  80

Ser Ala Ala Val Gly Gly Ile Thr Thr Ile Ile Glu Met Pro Ile Thr
                 85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285
```

```
Arg Ser Ala Glu Met Asn Ala Arg Leu Trp Glu Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
        370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
        435                 440                 445

Val Thr Arg His Asp Tyr Glu Ala Ser Lys
    450                 455         458
```

(2) INFORMATION FOR SEQ ID NO: 9:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 9

```
ATGTTTGACG TAATAGTTAA GAACTGCCGT ATGGTGTCCA GCGACGGAAT CACCGAGGCA    60

GACATTCTGG TGAAAGACGG CAAAGTCGCC GCAATCAGCT CGGACACAAG TGATGTTGAG   120

GCGAGCCGAA CCATTGACGC GGGTGGCAAG TTCGTGATGC CGGGCGTGGT CGATGAACAT   180

GCGAGCCGAA CCATTGACGC GGGTGGCAAG TTCGTGATGC CGGGCGTGGT CGATGAACAT   240

TCTGCGGCCG TGGGAGGCAT CACCACCATC ATCGAGATGC CGTTAACCTT CCCGCCCACC   300

ACCACTTTGG ACGCCTTCCT CGAAAAGAAG AAGCAGGCGG GCAGCGGTT GAAAGTTGAC    360

TTCGCGCTCT ATGGCGGTGG AGTGCCGGGA AACCTGCCCG AGATCCGCAA AATGCACGAC   420

GCCGGCGCAG TGGGCTTCAA GTCAATGATG GCAGCCTCAG TTCCGGGCAT GTTCGACGCC   480

GTCAGCGACG GCGAACTGTT CGAAATCTTC CAGGAGATCG CAGCCTGTGG TTCAGTCGTC   540

GTGGTCCATG CCGAGAATGA AACGATCATT CAAGCGCTCC AGAAGCAGAT CAAAGCCGCT   600

GGTCGCAAGG ACATGGCCGC CTACGAGGCA TCCCAACCAG TTTTCCAGGA GAACGAGGCC   660

ATTCAGCGTG CGTTACTACT GCAGAAAGAA GCCGGCTGTC GACTGATTGT GCTTCACGTG   720

AGCAACCCTG ACGGGGTCGA GCTGATACAT CAGGCGCAAT CCGAGGGCCA GGACGTCCAC   780

TGCGAGTCGG GTCCGCAGTA TCTGAATATC ACCACGGACG ACGCCGAACG AATCGGACCG   840

TATATGAAGG TCGCGCCGCC CGTCCGCTCA GCCGAAATGA ACGTCAGATT ATGGAACAA    900

CTTGAGAACG GGCTCATCGA CACCCTTGGG TCAGACCACG GCGGACATCC TGTCGAGGAC   960

AAAGAACCCG GCTGGAAGGA CGTGTGGAAA GCCGGCAACG GTGCGCTGGG CCTTGAGACA  1020
```

```
TCCCTGCCTA TGATGCTGAC CAACGGAGTG AATAAAGGCA GGCTATCCTT GGAACGCCTC        1080

GTCGAGGTGA TGTGCGAGAA ACCTGCGAAG CTCTTTGGCA TCTATCCGCA GAAGGGCACG        1140

CTACAGGTTG GTTCCGACGC CGATCTGCTC ATCCTCGATC TGGATATTGA CACCAAAGTG        1200

GATGCCTCGC AGTTCCGATC CCTGCATAAG TACAGCCCGT TCGACGGGAT GCCCGTCACG        1260

GGTGCACCGG TTCTGACGAT GGTGCGCGGA ACGGTGGTGG CAGAGAAGGG AGAAGTTCTG        1320

GTCGAGCAGG GATTCGGCCA GTTCGTCACC CGTCACGACT ACGAGGCGTC GAAGTGA           1377
```

(2) INFORMATION FOR SEQ ID NO: 10:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 10

```
Met Phe Asp Val Ile Val Lys Asn Cys Arg Met Val Ser Ser Asp Gly
              5                  10                  15

Ile Thr Glu Ala Asp Ile Leu Val Lys Asp Gly Lys Val Ala Ala Ile
         20                  25                  30

Ser Ser Asp Thr Ser Asp Val Glu Ala Ser Arg Thr Ile Asp Ala Gly
     35                  40                  45

Gly Lys Phe Val Met Phe Gly Val Val Asp Glu His Val His Ile Ile
 50                  55                  60

Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Ile Glu Met Pro Leu Thr
                 85                  90                  95

Phe Pro Pro Thr Thr Thr Leu Asp Ala Phe Leu Glu Lys Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Gln Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
        275                 280                 285
```

```
Arg Ser Ala Glu Met Asn Val Arg Leu Trp Gln Leu Glu Asn Gly
    290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
450                 455             458
```

(2) INFORMATION FOR SEQ ID NO: 11:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 11

```
ATGTTTGACG TAATAGTTAA GAACTGCCGT ATGGTGTCCA GCGACGGAAT CACCGAGGCA    60

GACATTCTGG TGAAAGACGG CAAAGTCGCC GCAATCAGCT CGGACACAAG TGATGTTGAG   120

GCGAGCCGAA CCATTGACGC GGGTGGCAAG TTCGTGATGC CGGGCGTGGT CGATGAACAT   180

GCGAGCCGAA CCATTGACGC GGGTGGCAAG TTCGTGATGC CGGGCGTGGT CGATGAACAT   240

TCTGCGGCCG TGGGAGGCAT CACCACCATC ATCGAGATGC CGTTAACCTT CCCGCCCACC   300

ACCACTTTGG ACGCCTTCCT CGAAAAGAAG AAGCAGGCGG GGCAGCGGTT GAAAGTTGAC   360

TTCGCGCTCT ATGGCGGTGG AGTGCCGGGA AACCTGCCCG AGATCCGCAA AATGCACGAC   420

GCCGGCGCAG TGGGCTTCAA GTCAATGATG GCAGCCTCAG TTCCGGGCAT GTTCGACGCC   480

GTCAGCGACG GCGAACTGTT CGAAATCTTC CAGGAGATCG CAGCCTGTGG TTCAGTCGCC   540

GTGGTCCATG CCGAGAATGA AACGATCATT CAAGCGCTCC AGAAGCAGAT CAAAGCCGCT   600

GGTCGCAAGG ACATGGCCGC CTACGAGGCA TCCCAACCAG TTTTCCAGGA GAACGAGGCC   660

ATTCAGCGTG CGTTACTACT GCAGAAAGAA GCCGGCTGTC GACTGATTGT GCTTCACGTG   720

AGCAACCCTG ACGGGTCGA GCTGATACAT CGGGCGCAAT CCGAGGGCCA GGACGTCCAC   780

TGCGAGTCGG GTCCGCAGTA TCTGAATATC ACCACGGACG ACGCCGAACG AATCGGACCG   840

TATATGAAGG TCGCGCCGCC CGTCCGCTCA GCCGAGATGA ACGTCAGATT ATGGGAACAA   900

CTTGAGAACG GGCTCATCGA CACCCTTGGG TCAGACCACG GCGGACATCC TGTCGAGGAC   960
```

-continued

```
AAAGAACCCG GCTGGAAGGA CGTGTGGAAA GCCGGCAACG GTGCGCTGGG CCTTGAGACA    1020

TCCCTGCCTA TGATGCTGAC CAACGGAGTG AATAAAGGCA GGCTATCCTT GGAACGCCTC    1080

GTCGAGGTGA TGTGCGAGAA ACCTGCGAAG CTCTTTGGCA TCTATCCGCA GAAGGGCACG    1140

CTACAGGTTG GTTCCGACGC CGATCTGCTC ATCCTCGATC TGGATATTGA CACCAAAGTG    1200

GATGCCTCGC AGTTCCGATC CCTGCATAAG TACAGCCCGT TCGACGGGAT GCCCGTCACG    1260

GGTGCACCGG TTCTGACGAT GGTGCGCGGA ACGGTGGTGG CAGAGAAGGG AGAAGTTCTG    1320

GTCGAGCAGG GATTCGGCCA GTTCGTCACC CGTCACGACT ACGAGGCGTC GAAGTGA       1377
```

(2) INFORMATION FOR SEQ ID NO: 12:

(i) SEQUENCE CHARACTERISTICS:
  (A) LENGTH: 458 amino acids
  (B) TYPE: amino acid
  (C) STRANDEDNESS: single
  (D) TOPOLOGY: linear (ii) MOLECULE TYPE: protein (xi) SEQUENCE DESCRIPTION: SEQ ID NO: 12

```
Met Phe Asp Val Ile Val Lys Asn Cys Arg Met Val Ser Ser Asp Gly
                 5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
 65                  70                  75                  80

Ser Ala Val Gly Gly Ile Thr Thr Ile Ile Glu Met Pro Leu Thr
                 85                  90                  95

Phe Pro Pro Thr Thr Thr Leu Asp Ala Phe Leu Glu Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ala Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

Gln Asp Val His Cys Glu Ser Gly Pro Gln Tyr Leu Asn Ile Thr Thr
            260                 265                 270

Asp Asp Ala Glu Arg Ile Gly Pro Tyr Met Lys Val Ala Pro Pro Val
```

```
            275                 280                 285
Arg Ser Ala Glu Met Asn Val Arg Leu Trp Glu Gln Leu Glu Asn Gly
    290                 295                 300

Leu Ile Asp Thr Leu Gly Ser Asp His Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
                340                 345                 350

Gly Arg Leu Ser Leu Glu Arg Leu Val Glu Val Met Cys Glu Lys Pro
                355                 360                 365

Ala Lys Leu Phe Glu Ile Tyr Pro Gln Lys Gly Thr Leu Gln Val Gly
370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
                420                 425                 430

Val Ala Glu Lys Gly Glu Val Leu Val Glu Gln Gly Phe Gly Gln Phe
                435                 440                 445

Val Thr Arg His Asp Tyr Glu Ala Ser Lys
                450                 455     458

(2) INFORMATION FOR SEQ ID NO: 13:

(i) SEQUENCE CHARACTERISTICS:
        (A) LENGTH: 1377 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 13

ATGTTTGACG TAATAGTTAA GAACTGCCGT ATGGTGTCCA GCGACGGAAT CACCGAGGCA        60

GACATTCTGG TGAAAGACGG CAAAGTCGCC GCAATCAGCT CGGACACAAG TGATGTTGAG       120

GCGAGCCGAA CCATTGACGC GGGTGGCAAG TTCGTGATGC CGGGCGTGGT CGATGAACAT       180

GCGAGCCGAA CCATTGACGC GGGTGGCAAG TTCGTGATGC CGGGCGTGGT CGATGAACAT       240

TCTGCGGCCG TGGGAGGCAT CACCACCATC ATCGAGATGC CGTTTACCTT CCCGCCCACC       300

ACCACTTTGG ACGCCTTCCT CGAAAAGAAG AAGCAGGCGG GGCAGCGGTT GAAAGTTGAC       360

TTCGCGCTCT ATGGCGGTGG AGTGCCGGGA AACCTGCCCG AGATCCGCAA AATGCACGAC       420

GCCGGCGCAG TGGGCTTCAA GTCAATGATG GCAGCCTCAG TTCCGGGCAT GTTCGACGCC       480

GTCAGCGACG GCGAACTGTT CGAAATCTTC CAGGAGATCG CAGCCTGTGG TTCAGTCGCC       540

GTGGTCCATG CCGAGAATGA AACGATCATT CAAGCGCTCC AGAAGCAGAT CAAAGCCGCT       600

GGTCGCAAGG ACATGGCCGC CTACGAGGCA TCCCAACCAG TTTTCCAGGA GAACGAGGCC       660

ATTCAGCGTG CGTTACTACT GCAGAAAGAA GCCGGCTGTC GACTGATTGT GCTTCACGTG       720

AGCAACCCTG ACGGGGTCGA GCTGATACAT CGGGCGCAAT CCGAGGGCCA GGACGTCCAC       780

TGCGAGTCGG GTCCGCAGTA TCTGAATATC ACCACGGACG ACGCCGAACG AATCGGACCG       840

TATATGAAGG TCGCGCCGCC CGTCCGCTCA GCCGAGATGA ACGTCAGATT ATGGGAACAA       900

CTTGAGAACG GGCTCATCGA CACCCTTGGG TCAGACCACG GCGGACATCC TGTCGAGGAC       960
```

```
AAAGAACCCG GCTGGAAGGA CGTGTGGAAA GCCGGCAACG GTGCGCTGGG CCTTGAGACA    1020

TCCCTGCCTA TGATGCTGAC CAACGGAGTG AATAAAGGCA GGCTATCCTT GGAACGCCTC    1080

GTCGAGGTGA TGTGCGAGAA ACCTGCGAAG CTCTTTGGCA TCTATCCGCA GAAGGGCACG    1140

CTACAGGTTG GTTCCGACGC CGATCTGCTC ATCCTCGATC TGGATATTGA CACCAAAGTG    1200

GATGCCTCGC AGTTCCGATC CCTGCATAAG TACAGCCCGT TCGACGGGAT GCCCGTCACG    1260

GGTGCACCGG TTCTGACGAT GGTGCGCGGA ACGGTGGTGG CAGAGAAGGG AGAAGTTCTG    1320

GTCGAGCAGG GATTCGGCCA GTTCGTCACC CGTCACGACT ACGAGGCGTC GAAGTGA       1377

(2) INFORMATION FOR SEQ ID NO: 14:

(i) SEQUENCE CHARACTERISTICS:
        (A) LENGTH: 458 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO: 14

Met Phe Asp Val Ile Val Lys Asn Cys Arg Met Val Ser Ser Asp Gly
                  5                  10                  15

Ile Thr Glu Ala Asp Ile Leu Val Lys Asp Gly Lys Val Ala Ala Ile
             20                  25                  30

Ser Ser Asp Thr Ser Asp Val Glu Ala Ser Arg Thr Ile Asp Ala Gly
         35                  40                  45

Gly Lys Phe Val Met Phe Gly Val Val Asp Glu His Val His Ile Ile
     50                  55                  60

Asp Met Asp Leu Lys Asn Arg Tyr Gly Arg Phe Glu Leu Asp Ser Glu
 65                  70                  75                  80

Ser Ala Ala Val Gly Gly Ile Thr Thr Ile Glu Met Pro Phe Thr
                 85                  90                  95

Phe Pro Pro Thr Thr Thr Leu Asp Ala Phe Leu Glu Lys Lys Gln
            100                 105                 110

Ala Gly Gln Arg Leu Lys Val Asp Phe Ala Leu Tyr Gly Gly Gly Val
        115                 120                 125

Pro Gly Asn Leu Pro Glu Ile Arg Lys Met His Asp Ala Gly Ala Val
    130                 135                 140

Gly Phe Lys Ser Met Met Ala Ala Ser Val Pro Gly Met Phe Asp Ala
145                 150                 155                 160

Val Ser Asp Gly Glu Leu Phe Glu Ile Phe Gln Glu Ile Ala Ala Cys
                165                 170                 175

Gly Ser Val Ala Val Val His Ala Glu Asn Glu Thr Ile Ile Gln Ala
            180                 185                 190

Leu Gln Lys Gln Ile Lys Ala Ala Gly Arg Lys Asp Met Ala Ala Tyr
        195                 200                 205

Glu Ala Ser Gln Pro Val Phe Gln Glu Asn Glu Ala Ile Gln Arg Ala
    210                 215                 220

Leu Leu Leu Gln Lys Glu Ala Gly Cys Arg Leu Ile Val Leu His Val
225                 230                 235                 240

Ser Asn Pro Asp Gly Val Glu Leu Ile His Arg Ala Gln Ser Glu Gly
                245                 250                 255

Gln Asp Val His Cys Glu Ser Gly Pro Gln Tyr Leu Asn Ile Thr Thr
            260                 265                 270
```

Asp Asp Ala Glu Arg Ile Gly Pro Tyr Met Lys Val Ala Pro Pro Val
            275                 280                 285

Arg Ser Ala Glu Met Asn Val Arg Leu Trp Glu Gln Leu Glu Asn Gly
            290                 295                 300

Leu Ile Asp Thr Leu Gly Ser Asp His Gly Gly His Pro Val Glu Asp
305                 310                 315                 320

Lys Glu Pro Gly Trp Lys Asp Val Trp Lys Ala Gly Asn Gly Ala Leu
                325                 330                 335

Gly Leu Glu Thr Ser Leu Pro Met Met Leu Thr Asn Gly Val Asn Lys
            340                 345                 350

Gly Arg Leu Ser Leu Glu Arg Leu Val Glu Val Met Cys Glu Lys Pro
            355                 360                 365

Ala Lys Leu Phe Glu Ile Tyr Pro Gln Lys Gly Thr Leu Gln Val Gly
            370                 375                 380

Ser Asp Ala Asp Leu Leu Ile Leu Asp Leu Asp Ile Asp Thr Lys Val
385                 390                 395                 400

Asp Ala Ser Gln Phe Arg Ser Leu His Lys Tyr Ser Pro Phe Asp Gly
                405                 410                 415

Met Pro Val Thr Gly Ala Pro Val Leu Thr Met Val Arg Gly Thr Val
            420                 425                 430

Val Ala Glu Lys Gly Glu Val Leu Val Glu Gln Gly Phe Gly Gln Phe
            435                 440                 445

Val Thr Arg His Asp Tyr Glu Ala Ser Lys
            450                 455     458

(2) INFORMATION FOR SEQ ID NO: 15:

(i) SEQUENCE CHARACTERISTICS:
        (A) LENGTH: 30 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 15

AGAACATATG TTTGACGTAA TAGTTAAGAA                                      30

(2) INFORMATION FOR SEQ ID NO: 16:

(i) SEQUENCE CHARACTERISTICS:
        (A) LENGTH: 28 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 16

AAAAGGATCC TCACTTCGAC GCCTCGTA                                        28

(2) INFORMATION FOR SEQ ID NO: 17:

(i) SEQUENCE CHARACTERISTICS:
        (A) LENGTH: 30 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 17

```
AGGCGACATA TGACCCTGCA GAAAGCGCAA                                    30
```

(2) INFORMATION FOR SEQ ID NO: 18:

(i) SEQUENCE CHARACTERISTICS:
        (A) LENGTH: 30 nucleotides
        (B) TYPE: nucleotide
        (C) STRANDEDNESS: single
        (D) TOPOLOGY: linear (ii) MOLECULE TYPE: nucleic acid (xi) SEQUENCE DESCRIPTION: SEQ ID NO: 18

```
ATGGGATCCC CGGTCAAGTG CCTTCATTAC                                    30
```

HYDANTOINASE VARIANTS WITH IMPROVED PROPERTIES AND THEIR USE FOR THE PRODUCTION OF AMINO ACIDS

This application claims the benefit of U.S. Provisional Application Nos. 60/126,923 filed Mar. 29, 1999 and 60/157,427 filed Oct. 4, 1999.

BACKGROUND OF THE INVENTION

1. Field of the Invention to previously isolated hydantoinases and their use in whole-cell catalysts to manufacture amino acids.

2. Description of Related Art

Hydantoin hydrolyzing enzymes, which will be referred here as 'hydantoinases', comprise a diverse class of enzymes having a wide range of specificities and biological functions. Some hydantoinases for example play an essential role in the reductive pathway of pyrimidine degradation (dihydropyrimidinases, EC 3.5.2.2) whereas others catalyze reactions in the purine degradation pathway (allantoinases, EC 3.5.2.5). Despite their functional diversity hydantoinases show significant sequence similarities and belong to a superfamily of amidohydrolases related to ureases as described by Holm, L., and Sander, C. (1997) An evolutionary treasure: Unification of a broad set of amidohydrolases related to ureases, *Proteins* 28:72–82; The alignment of sequences from the different hydantoinases was used to identify conserved residues that are important for catalytic function as described by May, O., Habenicht, A., Mattes, R., Syldatk, C. and Siemann, M. (1998) Molecular Evolution of Hydantoinases, *Biol Chem.* 379:743–747; and Kim, G. J. and Kim, H. S. (1998) Identification of the structural similarity in the functionally related amidohydrolases acting on the cyclic amide ring. *Biochem. J.* 330:295–302. Despite this knowledge that allows to identify equivalent amino acid residues of the different hydantoinases, knowledge about the function of other amino acid residues is limited. So far, no X-ray structure of hydantoinases was reported.

An important property of hydantoinases is their enantioselectivity which makes them valuable for the production of optically pure D- or L-amino acids. A detailed background of hydantoinases is provided in the published doctoral thesis of Oliver May entitled "The Hydantoinase from *Arthrobacter aurescens* DSM 3745 and its Relation to other Hydantoinases" (Institut fuer Bioverfahrenstechnik, Lehrstuhl Physiologische Mikrobiologie, Universitaet Stuttgart-1998).

In view of the importance of hydantoinases to the production of optically pure amino acids, there has been a concentrated effort to develop modified enzymes which have improved properties with respect to amino acid production. As a result of this effort, a number of microorganisms have been isolated and identified which produce hydantoinases with desirable enzymatic properties. U.S. Pat. No. 5,516,660 discloses microorganisms identified as DSM7329 and DSM 7330 which produce hydantoinases that are capable of producing L-alpha-amino acids from D-, L- and/or D,L-5-monosubstituted hydantoins. In U.S. Pat. No. 5,714,355, a mutant of the DSM 7330 microorganism is disclosed which has greater enzymatic activity than the parent organism by a factor of up to 2.7. The mutant (DSM 9771) was obtained by cultivating the parent DSM 7330 organism under selective pressure using L-carbamoylmethionine (L-CAM) as the sole source of nitrogen. Although the hydantoinases produced by the above-mentioned microoganisms are well-suited for at least some of their intended purposes, there still is a continuing need to develop new enzymes which exhibit even more desirable hydantoinase activity. In particular, there is a need to improve enantioselectivity as well as catalytic activity.

SUMMARY OF THE INVENTION

In accordance with the present invention, modified hydantoinases are provided which have enhanced enzymatic properties (better whole-cell catalysts) with respect to the hydantoinase produced by the microorganism DSM 9771 which is identified in U.S. Pat. No. 5,714,355. The DSM 9771 hydantoinase has an amino acid sequence which includes numbered positions ranging sequentially from 1 to 458 (SEQ. ID. NO. 2).

It was discovered that substitution of amino acids at one or more specific amino acid positions within the DSM 9771 enzyme resulted in the formation of enzymes having enhanced properties with respect to activity and enantioselectivity. The specific amino acid position numbers at which substitutions are made to achieve the modified hydantoinase enzymes in accordance with the present invention are positions Nos. 95, 154, 180, 251 and 295. As a further feature of the invention, specific amino acid substitutions at the various positions are identified to provide specific types of modified hydantoinases. The specific amino acid substitutions include I95F, I95L, V154A, V180A, Q251R and V295A. One or more of these specific substitutions were found to enhance the enzymatic activity and change the enantioselectivity of the "wild type" DSM 9771 hydantoinase. These changed enzyme properties were found to contribute to a significantly improved hydantoinase process by reducing the accumulation of the wrong enantiomer of the N-carbamoyl-amino acid.

Six specific modified hydantoinases are disclosed which have one or more of the above amino acid substitutions. The amino acid sequences for these modified hydantoinases are set forth in SEQ. ID. NOS. 4, 6, 8, 10, 12 and 14. These modified hydantoinases are also identified throughout the specification as 1CG7, 11DH7, 1BF7, 19AG11, 22CG2 and Q2H4, respectively.

It was further discovered that hydantoinases evolved for activity and/or enantioselectivity can dramatically improve the production of amino acids (i.e., L-methionine) using a whole cell catalyst comprising an evolved hydantoinase in addition to at least a carbamoylase.

The above discussed and many other features and attendant advantages of the present invention will become better understood by reference to the following detailed description when taken in conjunction with the accompanying drawings.

DETAILED DESCRIPTION OF THE INVENTION

Figure 1:
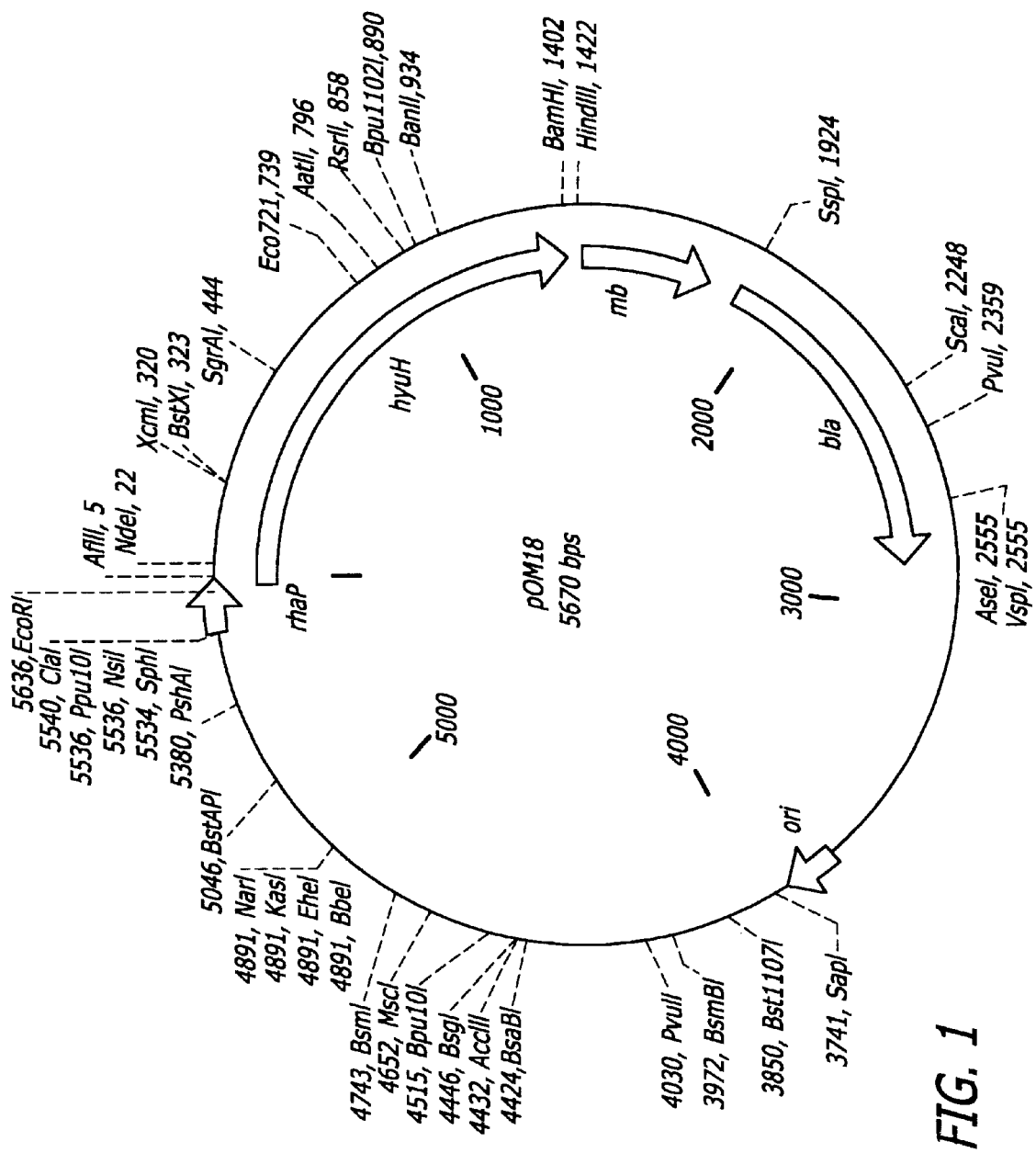
FIG. 1 is the restriction map of the vector used for expression of the hydantoinase gene (hyuH) from Arthrobacter sp. DSM9771.

The modified hydantoinases in accordance with the present invention were produced, identified and isolated using random mutagenesis procedures of the type described in U.S. Pat. Nos. 5,316935 and 5,906,930. Random mutagenesis protocols, which are also known as directed evolution procedures, are also described in Kuchner, O., Arnold, F. H. (1997) Directed Evolution of Enzyme Catalysts, *TIBTECH* 15:523–530; Chen, K. and Arnold F. (1991). Enzyme engineering for nonaqueous solvents—random mutagenesis to enhance activity of subtilisin E in polar organic media, *Bio/Technology* 9:1073–1077; Chen, K. and Arnold, F. (1993) Tuning the activity of an enzyme for unusual environments: sequential random mutagenesis of subtilisin E for catalysis in dimethylformamide, *Proc. Natl. Acad. Sci. USA* 90:5618–5622; and You, L. and Arnold, F. H. (1996). Directed Evolution of Subtilisin E in *Bacillus Subtilis* to Enhance Total Activity in Aqueous Dimethylformamide, *Protein Engineering*, 9, 77–83.

The random mutagenesis procedure used to identify and isolate the modified hydantoinases followed the same basic procedures as identified above. First, a large number of random mutations in the wild type nucleotide sequence (SEQ. ID. NO. 1) were generated. This library of nucleotide sequences where then used to express a large number of mutated enzymes. The library of mutated hydantoinases was then screened to identify those mutants with enhanced enzymatic activity and changed enantioselectivity.

The step of screening the first library of expressed amino acid sequences to identify desirable variants could have been accomplished using any number of suitable screening techniques which measure desirable enzyme properties. The screening method actually used was a pH-indicator assay which will be described in more detail below.

In accordance with the present invention, four enzymes having enhanced hydantoinase properties were identified as the result of the first round of random mutagenesis of the DSM 9711 nucleotide sequence (SEQ. ID. NO. 1). The first round mutant enzymes are 1CG7, 11DH7, 1BF7 and 19AG11. The nucleotide sequences for these first round mutants are set forth in SEQ. ID. NOS. 3, 5, 7 and 9, respectively. The corresponding amino acid sequences are set forth in SEQ. ID. NOS. 4, 6, 8 and 10, respectively.

A second round of random mutagenesis was conducted in which the 11 DH7 nucleotide sequence was randomly mutated to form a second library of mutants. A single mutant (22CG2) was identified which expressed a modified hydantoinase that exhibited desirable enzymatic properties. The 22CG2 enzyme is the same as the 11DH7 enzyme except that the 22CG2 mutant has an amino acid substitution at position 180.

The 22CG2 mutant was subjected to saturation mutagenesis in order to introduce all 20 different amino acids into amino acid position 95. 400 clones were screened and a mutant enzyme with enhanced enzymatic activity and higher (L)-selectivity was identified as Q2H4. The Q2H4 mutant is the same as the 22CG2 mutant except that phenylalanine is substituted for isoleucine at position 95.

As a result of the isolation and identification of the above identified mutants, it was established that improved hydantoinases may be obtained by modifying the DSM 9771 enzyme by substituting amino acids at positions 95, 124, 154, 180, 251 and 295. The substitutions may be made at one or more of the positions of SEQ. ID NO: 2. Table 1 sets forth preferred amino acid substitutions.

TABLE 1

| Amino Acid Position | Substitution | Abbreviation |
|---|---|---|
| 95 | Ile→Phe | I95F |
| 95 | Ile→Leu | I95L |
| 154 | Val→Ala | V154A |
| 180 | Val→Ala | V180A |
| 251 | Gln→Arg | Q251R |
| 295 | Val→Ala | V295A |

Amino acid substitutions other than those set forth in Table 1 are possible provided that the resulting hydantoinase exhibits desirable enzymatic properties. For example, other suitable amino acid substitutions for isoleucine at position 95 include Gly, Ala, Val, Leu, Phe, Tyr and Trp. For positions 154, 180 and 295, suitable alternative amino acid substitutions for valine include Ala and Gly. Suitable alternative amino acid substitutions at position 251 for glutamine include Arg, Lys and Asn. The amino acid substitutions may be made by saturation mutagenesis followed by screening of clones. The substitutions may also be made by chemical manipulation of the DSM 9711 enzyme or by conventional synthesis of peptides having the desired amino acid substitutions at the desired locations. It should be noted that the above listed amino acid substitutions are intended to be exemplary of preferred alternative substitutions at the various substitution sites. Substitutions of other amino acids are possible provided that the enzymatic activity of the resulting protein is not destroyed. The usefulness of a particular amino acid substitution at positions 95, 154, 180, 251 and 295 can be determined by routine pH screening as described below.

The amino acid substitutions described above may be made at equivalent positions in other hydantoinases. "Other hydantoinases" refers to enzymes that catalyze the hydrolysis of any 5'-mono- or disubstituted hydantoin derivative to yield the derived N-carbamoyl-amino acid and might have between 20 and 100% amino acid sequence identity to the hydantoinase from Arthrobacter sp. DSM 9771 which can be determined by sequence alignment algorithm such as BLAST (Altschul, S. F., Gish, W., Miller, W., Myers, E. W. & Lipman, D. J. (1990) "Basic local alignment search tool." *J. Mol. Biol.* 215:403–410).

Amino acid positions are numbered in a linear order (starting at the start codon) and not according to their functional and structural context. Therefore amino acid residues that contribute in the same way to an enzyme function of different hydantoinases do not necessarily have the same amino acid position number due to deletion or insertion events in the homologous enzyme. "Equivalent positions" of hydantoinases therefore refers to amino acid positions that contribute in the same way to a function (activity or enantio-selectivity) as the amino acids identified in our evolution experiment. If the amino acid sequence identity of different hydantoinases is high, for example higher than 60%, and the amino acid position is located in a conserved region without sequence gaps, equivalent positions can be determined by sequence alignment using for example the BLAST algorithm. If the amino acid sequence identity is low, for example lower than 60%, and the amino acid position is located in a non-conserved region, or near gaps without being surrounded by regions of conserved amino acids, other methods such as structure alignments can be used if x-ray structures are available (Mizuguchi, K., Go, N., Seeking significance in 3-dimensional protein-structure comparisons. *Cur. Opin. Struc. Biol.* 5:377–382 (1995)). Here, backbone atoms are structurally aligned and equivalent positions can be found based on the relative locations of the amino acid residues of the structures.

An amino acid position that is identified for example by directed evolution to contribute to a specific function can often be occupied by different amino acid residues, not just the one that was identified by random point mutagenesis. Some substitutions will destroy the function, some of them will not change the function, and yet others will improve the function. With known methods, such as site saturation mutagenesis, one can easily identify amino acids that contribute in the same way to a function or even improve it by replacing the found amino acid residue with all possible amino acid residues (Miyazaki, K., Arnold, F., Exploring nonnatural evolutionary pathways by saturation mutagenesis: rapid improvement of protein function. *J. Mol. Evol.* 49:1716–1720). Even non-natural amino acids can be introduced at the identified site using a stop codon and a suppresser tRNA linked to a non-natural amino acid (Bain, J. D., Glabe, C. G., Dix, T. A., Chamberlain, A. R., Diala, E. S., Biosynthetic Site-Specific Incorporation Of A Non-Natural Amino-Acid Into A Polypeptide. *JACS* 111:8013–8014 (1989)).

Six modified hydantoinases in accordance with the present invention are listed in Table 2. Table 2 also lists the amino acid substitutions with respect to the DSM 9771 sequence (SEQ. ID. NO. 2) for each modified enzyme which is identified.

TABLE 2

| Hydantoinase Variant | Amino Acid Substitution |
| --- | --- |
| 1CG7 (SEQ. ID. NO. 4) | V154A |
| 11DH7 (SEQ. ID. NO. 6) | I95L + O251R |
| 1BF7 (SEQ. ID. NO. 8) | V295A |
| 19AG11 (SEQ. ID. NO. 10) | I95L |
| 22CG2 (SEQ. ID. NO. 12) | I95L + V180A + Q251R |
| Q2H4 (SEQ. ID. NO. 14) | I95F + V180A + Q251R |

The modified hydantoinases of the present invention may be used in the same manner as other hydantoinases to produce optically pure D- and L-amino acids. For example, see *Biocatalytic Production of Amino Acids and Derivatives* (Rozzell, J. D. and Wagner, F. eds.) (1992) Hanser Publisher, NY, at pages 75–176, for a description of the use of hydantoinases in the production of optically pure amino acids from DL-5-monosubstituted hydantoins. The general use of hydantoinases is also described in Enzyme catalysis in organic synthesis (Dranz, K. and Waldmann, H. eds.) 1995, VCH-Verlag, Weinheim, at pages 409–431; and Wagner, T. et al. (1996) Production of 1-methionine from d,1-5-(2-methylthioethyl) hydantoin by resting cells of a new mutant strain of Arthrobacter species DSM 7330, *Journal of Biotechnology* 46:63–68.

Amino acids referred to in the present invention are all natural or unnatural amino acids, wherein the amino acids are deemed to be a primary amine connected to carboxylic acid group via one intermediate C-atom ($\alpha$-C-atom). This C-atom bears only one further residue. Preferred unnatural amino acids are disclosed in DE 19903268.8. Preferred natural amino acids are those mentioned in Beyer-Walter, Lehrbuch der Organischen Chemie, 22. Auflage, S. Hirzel Verlag Stuttgart, S.822–827. Among those amino acids presented above alanine, leucine, isoleucine, methionine, valine, tert.-leucine or neopentyl glycine are not preferably transformed in a process utilizing the modified hydantoinase.

To transform hydantoins directly to the amino acids by enzymes it is preferred to use a whole-cell catalyst which includes the hydantoinase of the invention accompanied with a carbamoylase. A hydantoin racemase can also be used in addition to the hydantoinase and carbamoylase.

The hydantoinase can be used within this process either in their free or immobilized form. Also the carbamoylase and hydantoin racemase may be immobilized, too. Techniques to immobilize enzymes are well known to the skilled worker. Preferred methods are mentioned in Bhavender P. Sharma, Lorraine F. Bailey and Ralph A. Messing, Immobilisierte Biomaterialien-Techniken und Anwendungen, Angew. Chem. 1992, 94, 836–852; Dordick et al., J. Am. Chem. Soc. 194, 116, 5009–5010; Okahata et al., Tetrahedron Lett. 1997, 38, 1971–1974; Adlercreutz et al., Biocatalysis 1992, 6, 291–305; Goto et al., Biotechnol. Prog. 1994, 10, 263–268; Kamiya et al., Biotechnol. Prog. 1995, 11, 270–275; Okahata et al., Tibtech, February 1997, 15, 50–54; Fishman et al., Biotechnol. Lett. 1998, 20, 535–538).

The transformation discussed can be conducted in a batch process or continuous manner. Advantageously, an enzyme-membrane-reactor is used as the reaction vessel (Wandrey et al. in Jahrbuch 1998, Verfahrenstechnik und Chemieingenieurwesen, VDI S. 151ff.; Wandrey et al. in Applied Homogeneous Catalysis with Organometallic Compounds, Vol. 2, VCH 1996, S.832 ff.; Kragl et al., Angew. Chem. 1996, 6, 684f.).

A further embodiment of the present invention is directed to a whole cell catalyst comprising a gene encoding for a carbamoylase, an optional racemase and a hydantoinase wherein the hydantoinase is considered to be according to the modified hydantoinase of the invention.

Advantageously, a bacteria is used as a cell, because of high reproduction rates and easy growing conditions to be applied. There are several bacteria known to the skilled worker which can be utilized in this respect. Preferably *E. coli* can be used as the cell and expression system in this regard (Yanisch-Perron et al., *Gene* (1985), 33, 103–109). Another aspect of the invention is a process for the production of enantiomerically enriched amino acids, which utilizes a whole cell catalyst according to the invention.

It is further preferred in this respect that amino acids like methionine, threonine, lysine or tert.-leucine are produced by the aid of the whole cell catalyst.

The transformation discussed in this instance can be conducted in a batch process or continuous manner. Advantageously, an enzyme-membrane-ractor is used as the reaction vessel (Wandrey et al. in Jahrbuch 1998, Verfahrenstechnik und Chemieingenieurwesen, VDI S. 151ff.; Wandrey et al. in Applied Homogeneous Catalysis with Organometallic Compounds, Vol. 2, VCH 1996, S832 ff.; Kragl et al., Angew. Chem. 1996, 6, 684f; DE 19910691.6).

There is a further aspect of the invention, which is directed to a process for the production of a whole cell catalyst of the invention. The process is preferably conducted by using expression vectors pOM17, pOM18, pOM20, pOM22 and/or pOM21. In addition primers of SEQ. NO. 17, SEQ. NO. 18, SEQ. NO. 15 and/or SEQ. NO. 16 are used with regard to the production of the whole cell catalyst.

Examples of Practice are as follows:

EXAMPLE 1

The following example provides additional details regarding the procedures used to identify and isolate the modified hydantoinases in accordance with the present invention.

The hydantoinase from Arthrobacter sp. DSM 9771 (U.S. Pat. No. 5,714,355) was cloned by polymerase chain reaction (PCR). The nucleotide sequence was determined and compared to other hydantoinases from closely related Arthrobacter strains. The nucleotide and amino acid sequences for the hydantoinase are set forth in SEQ. ID. NOS. 1 and 2, respectively. The cloned enzymes from Arthrobacter sp. DSM 9771 share about 97.5% identity based on their nucleotide sequence (corresponding to 7 amino acid changes) with the enzymes from Arthrobacter aurescens DSM 3747 and DSM 3745. The enzymes were expressed in E.coli JM109 using a rhamnose inducible vector construct which was provided by the Institute of Industrial Genetics, Universitait Stuttgart (Germany). The restriction map is set forth in FIG. 1.

The hydantoinase was subjected to random mutagenesis using error-prone PCR. Approximately 10,000 clones were screened using a pH-indicator assay as described below:

1. Seed culture plates: plates containing 100 µl/well LBamp were inoculated with single colonies/well and incubated for 24 hours at 30° C., 250 rpm.
2. Main culture plates: cells from seed culture plates were transferred with a 96-pin replicator into plates containing 200 µl LBamp+0.2% rhamnose. Plates were incubated for 24 hours at 30° C., 250 rpm.
3. Assay: using a pipetting robot, the culture of each well was mixed by pipetting up and down (3x) and transferred (75 µl each) into two fresh plates. The two plates are filled with 100 µl/well freshly prepared substrate solution (80 mM D-MTEH and L-MTEH respectively, in 0.05 g/l cresol red pH 8.6). The absorbance at 580 nm is measured immediately after the substrate was added to the plate and after 3 hours incubation at room temperature. The activity was calculated as follows:

Activity=(A580(0h)-A580(3h))/((A580(0h)-0.8))(Rem:0.8 is the absorbance without cells)

For screening purposes, the ratio of activities for the D- and L-enantiomers is taken as an indicator for changed enantioselectivity.

Since the ratio of activities for different enantiomers in the screening tests is only a first hint of enantioselectivity, the identified mutants were confirmed by chiral HPLC using the racemic substrate as follows. 2 ml overnight cultures were added to 2 ml 80 mM DL-MTEH in 0.1M Tris pH8.5 and incubated at 37° C. After 1h and 2h respectively, the reaction mixture was centrifuged for 2 minutes, 14000 rpm. 20 µl of the supernatant was applied onto the HPLC column and the various fractions eluted.

About 2% of the population showed a significantly higher (>50%) activity compared to wild-type DSM 9771. Although a considerable number of those clones might be false positives due to common variation of expression level in a population, about 50% of rescreened clones were indeed higher activity mutants. The high number indicates that hydantoinase has a large evolutionary potential (its activity and enantioselectivity can be therefor improved). This can be rationalized since a high Km value (about 15 mM), a rather low specific activity (about 12U/mg) and a low expression level (<10% of total protein) leaves room for improvements of this enzyme.

Table 3 shows the results of the tested mutants. Mutant 1CG7 shows a dramatic increase of (D-) selectivity. Compared to wild-type, the enantiomeric excess of the product is 4 times increased. The enantioselectivity of clone 11DH7 and 19AG11 was changed into the opposite direction since both mutants are absolutely non-selective. The activity mutant 1BF7 possesses the same enantioselectivity as wild-type.

TABLE 3

| Clone | Conversion | enantiomeric excess [%] |
|---|---|---|
| wild-type | 42% after 2 hours | 19 |
| 1CG7 | 42% after 2 hours | 90 |
| 11DH7 | 42% after 2 hours | 0 |
| 19AG11 | 37% after 2 hours | 0 |
| 1BF7 | 45% after 1 hour | 19 |

All of the mutants were sequenced and the nucleotide and amino acid sequences established as set forth in Table 4.

TABLE 4

|  | Nucleotide Sequence (SEQ. ID. NO.) | Amino Acid Sequence (SEQ. ID. NO.) |
|---|---|---|
| 1CG7 | 3 | 4 |
| 11DH7 | 5 | 6 |
| 1BF7 | 7 | 8 |
| 19AG11 | 11 | 12 |

A second round of random mutagenesis was conducted using the first generation mutant 11 DH7 as the parent.

Two different libraries with different error rates (20% and 50% inactive clones) were produced and 10,000 clones of each libarry were screened using the above-described pH-indicator method. None of the screened clones showed significantly higher L-selectivity but mutants with improved activity and higher D-selectivity were found. One mutant (22CG2) differing in only one amino acid (V180A) from the parent was found to be 4-fold more active compared to parent 11DH7.

Figure 2:
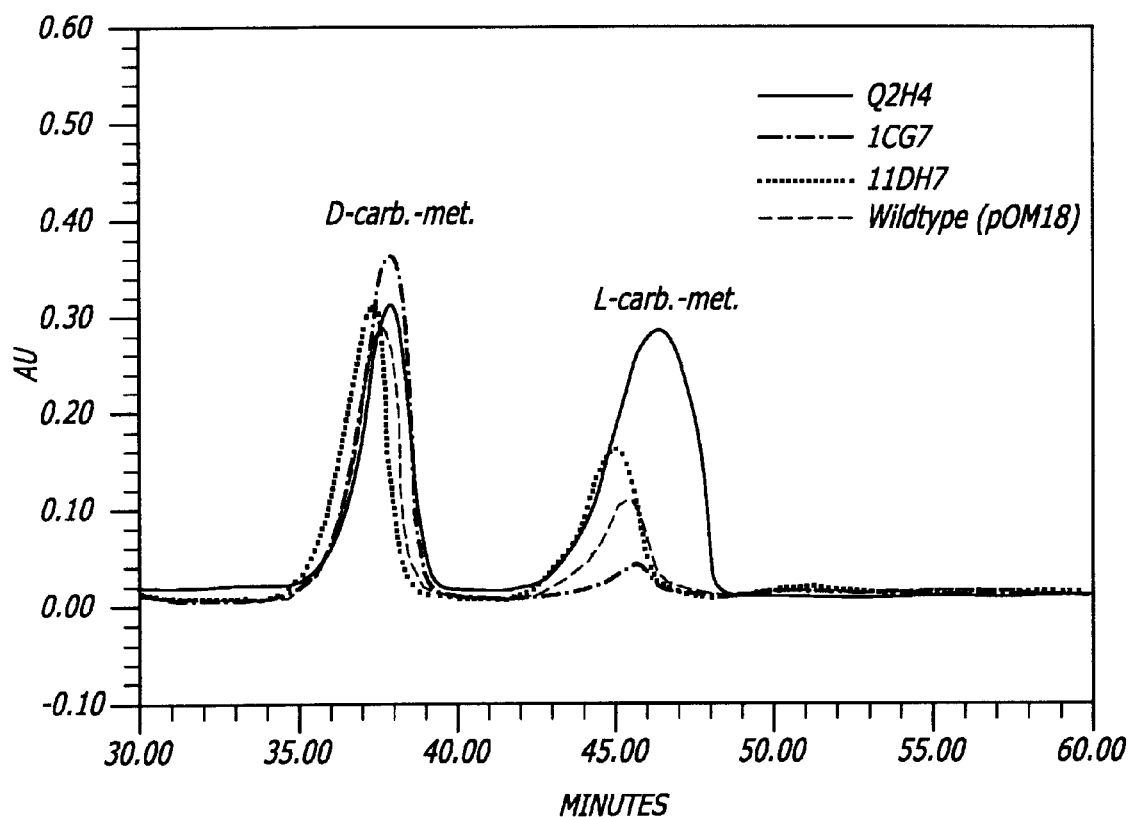
FIG. 2 is a chromatogram showing the results of the separation of N-carbomoyl-methionine enantiomers produced by mutants Q2H4, 11DH7 and 1CG7 as compared to the DSM 9771 hydantoinase.

Sequencing of the first generation mutants 11DH7 and 19AG11 revealed a single mutation (I95L) is responsible for their decreased D-selectivity. Introducing all 20 different amino acids into amino acid position 95 of mutant 22CG2 by saturation mutagenesis and screening of about 400 clones revealed a new mutant (Q2H4) with significantly improved L-selectivity (ee$_L$=20%) and 1.5-fold improved activity compared to its parent 22CG2. The results of HPLC analysis for enantioselectivity are shown in FIG. 2. The nucleotide and amino acid sequences for 22CG2 are set forth in SEQ. ID. NOS. 11 and 12, respectively. The nucleotide and amino acid sequences for Q2H4 are set forth in SEQ. ID. NOS. 13 and 14, respectively.

Figure 4:
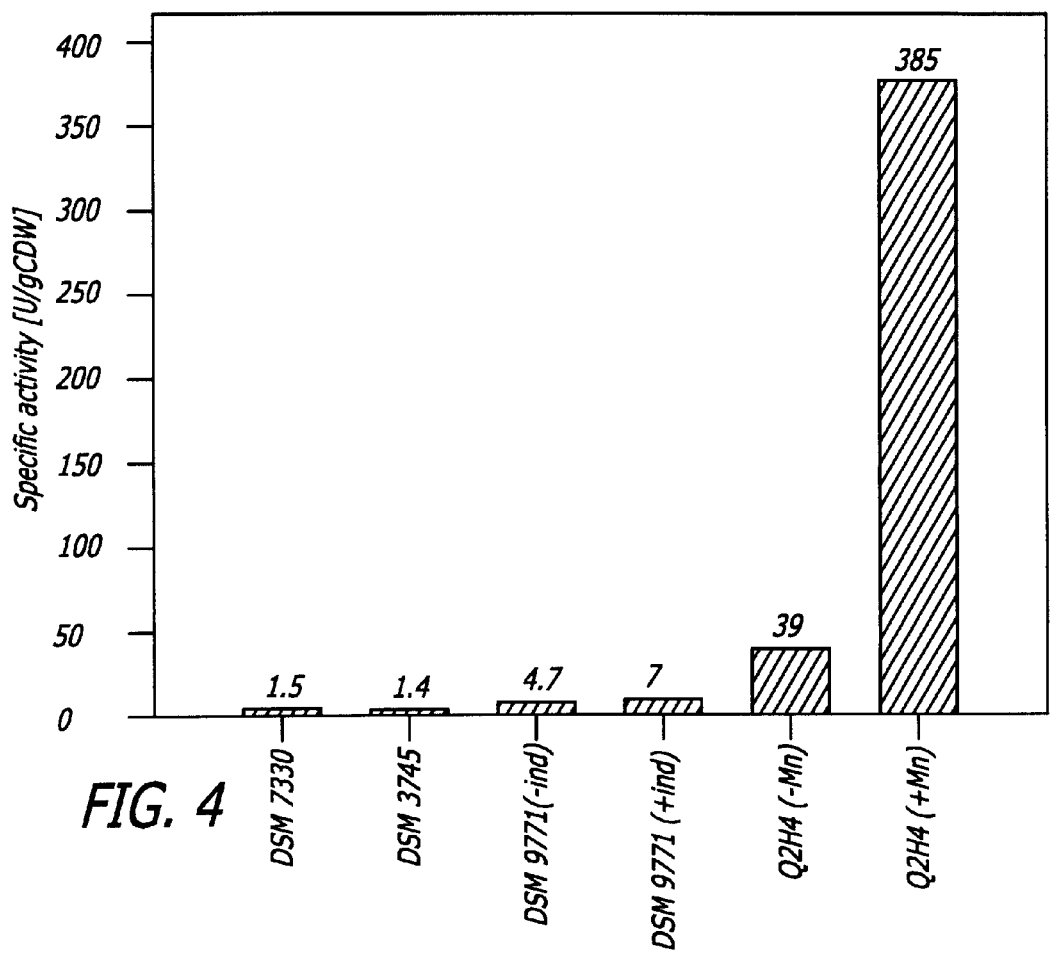
FIG. 4 is a chart which shows enzymatic activity of different Arthrobacter strains and mutant Q2H4 of the present invention.

In addition to the improvements provided by the mutants described above, the activity of the whole cell catalyst could be increased by a factor of 10 by addition of 1 mM manganese to the growth medium and to the substrate solution. Under those conditions the activity of mutant 22CG2 was determined to be about 380 U/gCDW which is a 50-fold increase in activity compared to the activity described for Arthrobacter sp. DSM 9771. A comparison of the activity of mutant Q2H4 with other strains is given in FIG. 4.

Figure 3:
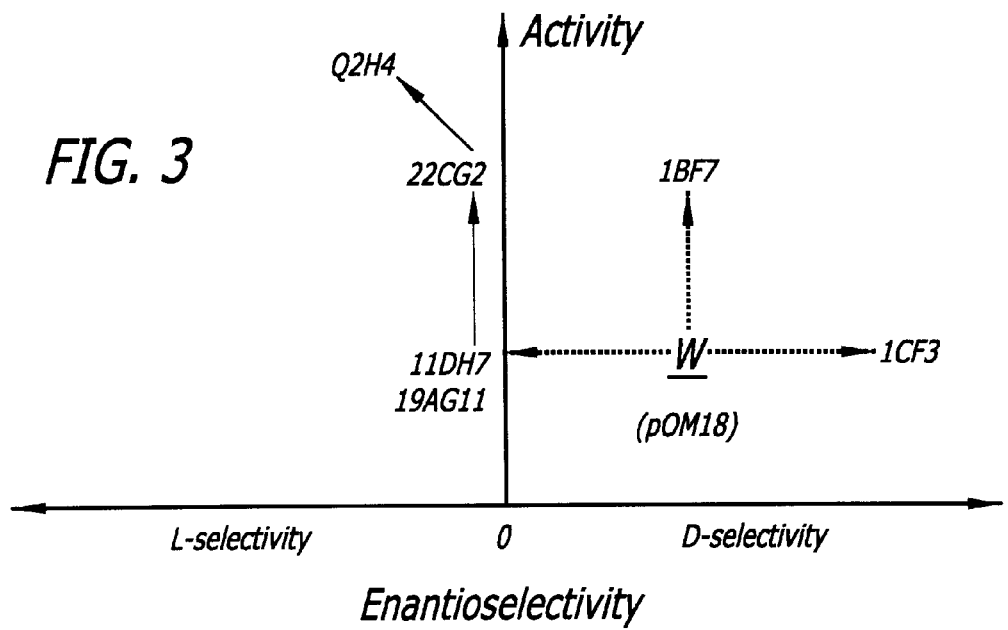
FIG. 3 is a chart which depicts the relative improvements in enzymatic activity and enantioselectivity which is provided by the mutant enzymes of the present invention with respect to the DSM 9771 hydantoinase (W).

A summary of the enzymatic activities of the various modified enzymes with respect to the parent DSM 9771 is set forth in FIG. 3. As can be seen from FIG. 3, all of the modified enzymes identified in accordance with the present invention have activities and/or enantioselectivity which are better than the unmodified DSM 9771 hydantoinase. When tested under standard conditions by HPLC, the Q2H4 mutant showed inverted enantioselectivity for the hydrolysis of D,L-MTEH. Q2H4 produced N-carbamoyl-L-methionine with an enantiomeric excess (ee) of 20% at about 30% conversion. In addition, the Q2H4 mutant was approximately 1.5-fold more active than its parent 22CG2.

EXAMPLE 2

In a further example, L-methionine was produced with a recombinant whole cell catalyst. Recombinant whole cell catalysts were prepared by co-expressing the evolved or wild-type hydantoinase with a hydantoin racemase and a L-carbamoylase in E.coli as follows.

Strains and expression vectors. The L-carbamoylase and hydantoinase expression vector pOM17 and pOM18 were constructed by PCR amplification of the hyuC and hyuH gene, respectively, from Arthrobacter sp. DSM 9771 using the following primer: for hyuC-amplification: 5'-AGGCGACATA-TGACCCTGCAGAAAGCGCAA-3' (SEQ. ID. NO. 17), 5'-ATGGGATCCCCGGT-CAAGTG CCTTCATTAC-3' (SEQ. ID. NO. 18); for hyuH-amplification: 5'-AGAACATATGTTTGACGTAATAG TTAAGAA-3' (SEQ. ID. NO. 15), 5'-AAAAGGAT-CCTC ACTTCGACGCCTCGTA-3' (SEQ. ID. NO. 16). The amplified fragments were cleaved with the restriction enzymes NdeI and BamHI and inserted using the same restriction enzymes downstream the rha BAD promotor (rhamnose promotor) into the vector pJOE2702 (Volff, J.-N., Eichenseer, C., Viell, P., Piendl, W. & Altenbuchner, J. (1996) Nucleotide sequence and role in DNA amplification of the direct repeats composing the amplificable element AUDI of Streptomyces lividans 66. Mol. Microbiol. 21, 1037–1047). The co-expression plasmid pOM20 comprising the L-carbamoylase and hydantoinase gene, both separately under the control of a rhamnose promotor, was derived from Plasmid pOM17 and pOM18. pOM17 was digested by SalI and treated with the Klenow fragment to form blunt ends. pOM18 was digested by BamHI and also treated with the Klenow fragment to form blunt ends. Both fragments were subsequently digested from HindIu. The 1521 kb-fragment comprising the carbamoylase gene and rhamnose promotor derived from pOM17 was ligated with the 5650 kb-fragment of the digested pOM18 to yield pOM20. Mutations of the L-selective hydantoinase were introduced into pOM20 using the restriction enzymes RsrII and KasI which yielded pOM22. The racemase expression vector pOM21 was derived from pACYC184 (Rose, R.E. The nucleotide sequence of pACYC184. Nucleic Acids Res. 16, 355 (1988)) and carries a chloramphenicol selection marker and the racemase gene hyuR from Arthrobacter sp. DSM3747 under the control of the rhamnose promotor. All plasmids were routinely transformed into E.coli JM109 (Yanisch-Perron, C., Viera, J. & Messing, J. (1984) Improved M13 phage cloning vectors and host strains: nucleotide sequences of the M13 mp18 and pUC vectors. Gene 33, 103–109). The hydantoin converting pathway was installed in E.coli JM109 by transformation of pOM20 and pOM22, respectively into E.coli JM109 (pOM21). Cells were either grown in LB liquid medium or on LB-agar plates (Luria. S. E., Adams, J. N. & Ting, R. C. (1960) Transduction of lactose-utilizing ability among strains of Escherichia coli and Shigella dysenteriae and properties of phage particles. Virology 12, 348–390), both supplemented with the respective antibiotics for the growth and expression medium (100 µg/ml ampicillin, 50 µg/ml chloramphenicol) and addition of 2 mg/ml rhamnose for the expression medium.

Error-prone PCR. Random mutagenesis of the hydantoinase gene was performed in a 100 µl reaction mix containing 0.25 ng of plasmid DNA as template, Boehringer PCR buffer (10 mM Tris, 1.5 mM $MgCl_2$, 50 mM KCl, pH 8.3), 200 µM dATP, 200 µM dTTP, 200 µM dGTP, 200 µM dCTP, 50 pmol of each primer, and 2.5U Taq polymerase (Boehringer). After 30 cycles, the 1667 amplification product was extracted from gel using the QiaexII gel-extraction kit (Qiagen, Valencia, Calif.) and subcloned into vector pJOE2702 using the EcoRI and HindIII restriction sites. Religation frequency of alkaline phosphatase treated vector was below 1%.

Saturation mutagenesis. For randomization of the codon for amino acid position 95, the QuickChange™ protocol (Stratagene, La Jolla, Calif.) was used. About 10 ng plasmid from clone 22CG2 were amplified by PCR using two complimentary oligonucleotides (5'-CATCGAGATGCCGNNNACCTTCCCG-CCCAC-3', 5-GTGGGCGGGAAGGTNNNCGGCATCTGATG-3'). After PCR amplification the reaction mixture was treated for 2 hours with 20 U of the restriction enzyme Dpnl. Transformation of 10 µl DpnI digested reaction imixture into competent cells yielded a library of more than 2000 mutants of which about 400 were screened.

Preparation of library and screening. Single colonies of transformed E.coli were transferred into 384-well plates (master plates) using the robot system Qbot (Genetix, Dorset, UK). After 20 hour growth at 37° C. plates were stored at –80° C. For subsequent screening, plates were thawed and replicated into 96-well plates containing 200 µl per well inductor medium. A Biomek 1000 pipetting workstation (Beckman, Fullerton, Calif.) was used to divide the 24 hours at 30° C. incubated plate into two fresh 96-well plates one containing 100 µl 80 mM L-MTEH the other 100 µl 80 mM D-MTEH in 50 mg/l cresol red solution adjusted to pH 8.5. Initial absorbance at 580 nm and after 3 hours incubation at room temperature were measured using a THERMOmax plate reader (Molecular Devices, Sunnyvale, Calif.). Activity was calculated from the difference of initial and absorbance after 3 hours incubation divided by the cell density of each well. For the saturation mutagenesis library incubation time was reduced to 1.5 hours. The ratio of activity towards the L- and D-enantiomer was taken as a first indicator for enantioselectivity. Identified clones were then tested using the racemic substrate under conditions described below.

Characterization of activity and enantioselectivity. Plasmid of mutant found to be positive in the screen was sequenced and retransformed into E.coli. A culture of retransformed E.coli was grown for 16–18 hours (until OD10) in inductor medium supplemented with 1 mM $MnCl_2$. 2 ml substrate solution consisting of 80 mM D,L-MTEH, 0.1M Tris pH 8.5, 1 mM $MnCl_2$ (pre-incubated at 37° C.) were added to 2 ml cell culture (OD600–7). The reaction mixture was immediately incubated at 37° C. in a water bath. After different time periods (as specified in the text) 1 ml samples were taken and centrifuged for 5 minutes at 14,000 rpm. 20 µl of supernatant were analyzed by chiral HPLC using a column manufactured by Degussa-Huels AG. Activity was calculated from the amount of produced N-carbamoyl-D,L-methionine and expressed as U/ml cell culture of U/mg cell dry weight (CDW) were 1U is the amount of whole-cell catalyst to produce 1 μmol N-carbamoyl-D,L-methionine in one minute under stated reaction conditions. Enantioselectivity of the hydantoinase and its mutants were compared by calculating the percentage of $ee_D$ ((D−L)/(D+L)) and $ee_L$ ((L−D)/(L+D)) respectively for the product at various extents of conversion. A conventional determination of E (enantiomeric ratio) from ee-values and the extent of conversion as described by Chen et al. (Chen, C. S., Fujimoto, Y., Girdaukas, G. & Sih, C. J. (1982) Quantitative analysis of biochemical kinetic resolutions of enantiomers. *J Am. Chem. Soc.* 104, 7294–7299) is not possible because of the fast racemization of the substrate.

Conversion of D,L-MTEH into L-met. 8 mg cell dry mass of *E.coli* JM109 (pOM20 & pOM21) and *E.coli* JM109 (pOM 22 & pOM21) were added to 4 ml 100 mM D,L-MTEH in 0.1 M Tris pH 7.8 supplemented with 1 mM $MnCl_2$. The reaction mixture was incubated at 37° C. Samples were analyzed after indicated periods of time and analyzed by HPLC for MTEH, D,L-C met, and D,L-met as described in Völkel, D. & Wagner, F. Reaction (1995) mechanism for the conversion of 5-monosubstituted hydantoins to enantiomerically pure L-amino acids. *Ann. NY Acad. Sci.* 750, 1–9. The optical purity of the compounds was analyzed by chiral HPLC as described above.

Figure 5:
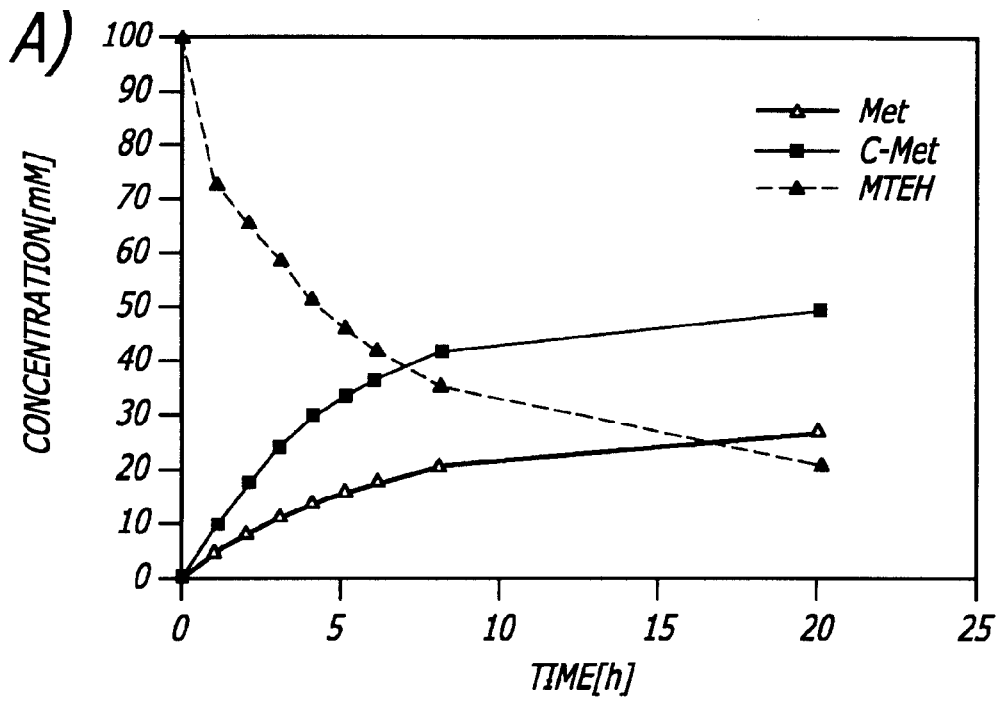
FIG. 5 is two charts showing the time course of the hydrolysis of 100 mM D,L-MTEH in 0.1M Tris pH 7.8, 37° C. with 8 mg cell dry mass of A) E.coli JM109 (pOM20/pOM21) (wildtype pathway) and B) E.coli JM109 (pOM22/pOM21) (pathway with evolved hydantoinase from Q2H4).
Figure 5:
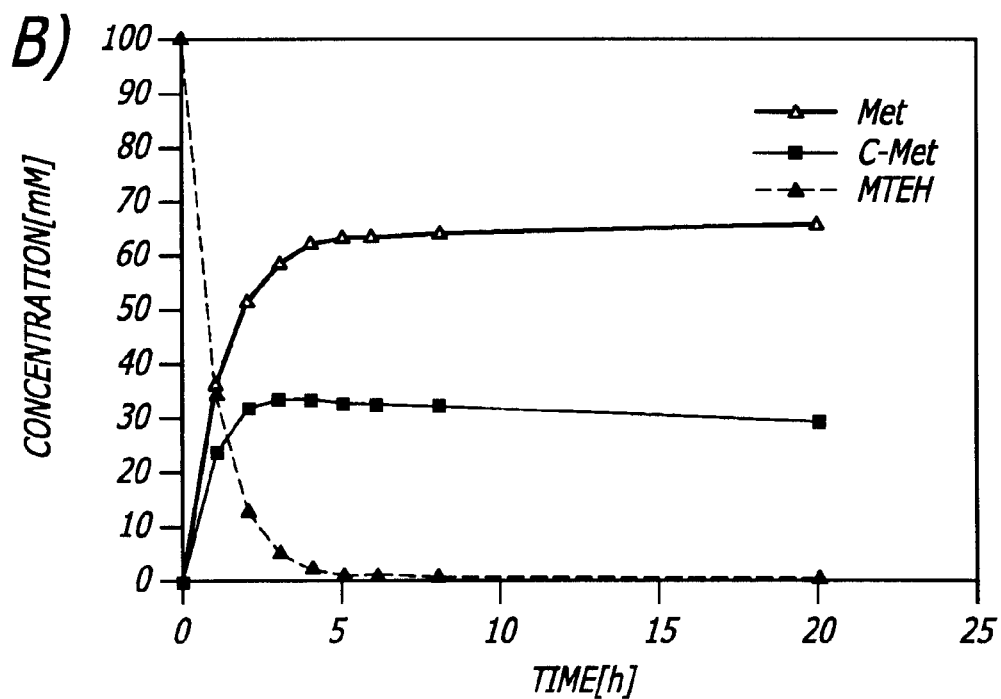

As shown in FIG. 5, the conversion of D,L-MTEH into L-met is significantly improved for the catalyst with the evolved hydantoinase. After three hours, approximately 60 mM L-met was produced from 100 mM D,L-MTEH, whereas the whole cell catalyst with the wild-type pathway produced only 10 mM of the amino acid. The concentration of the D-C met intermediate was reduced by a factor of 4 and the productivity for the production of L-amino acid was 8-fold increased during the first hour of the reaction.

EXAMPLE 3

Figure 6:
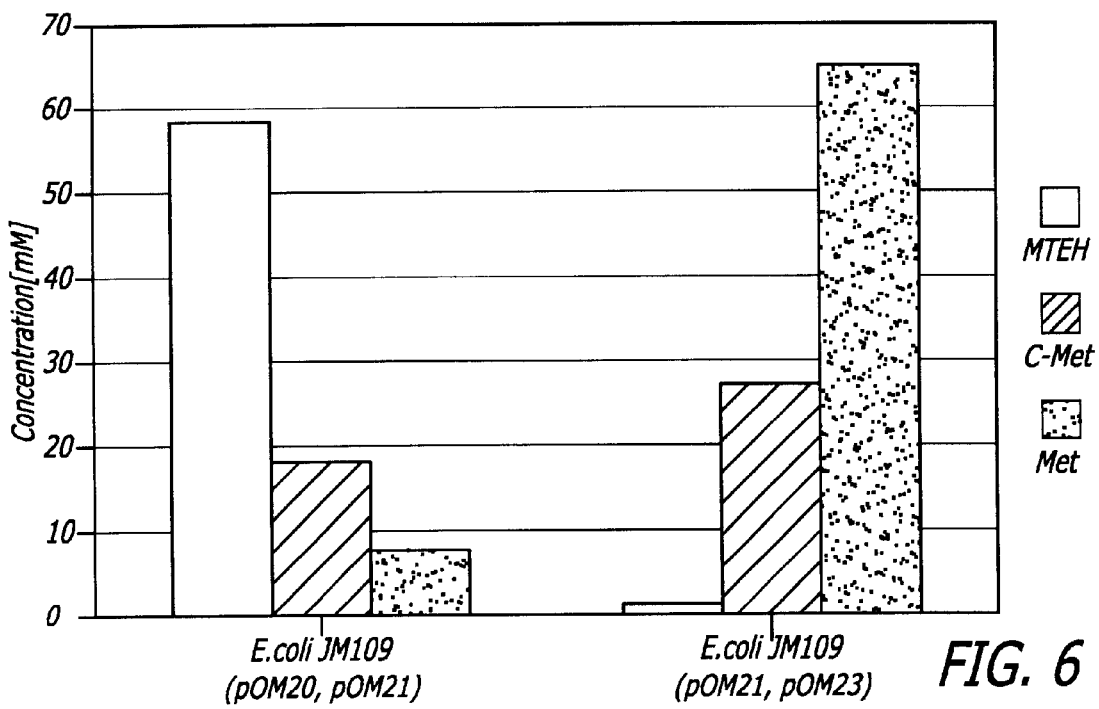
FIG. 6 is a chart showing a comparison of the hydrolysis of 100 mM D,L-MTEH in 0.9% (w/v) NaCl, 1 mM $MnCl_2$, pH 7.8 with 25 g/l E.coli JM109 (pOM20, pOM21) and E.coli JM109 (pOM21, pOM23) after 1 hour reaction time.

The following example shows that production of L-methionine was significantly improved with an evolved hydantoinase of mutant 22CG2 which has improved activity and is not enantioselective (0% enantiomeric excess at 42% conversion, see Table 3). Mutations of the evolved hydantoinase from mutant 22CG2 were introduced into pOM20 as previously described using the restriction enzymes Rsrll and Kasl, which yielded pOM23. This co-expression vector was transformed into *E.coli* JM109 (pOM21). The resulting whole cell catalyst *E.coli* JM109 (pOM21/pOM23) and *E.coli* JM109 (pOM21/pOM20) were used for conversion of D,L-MTEH into methionine. 125 mg cell dry mass of the respective cells were added to 5 ml substrate solution (100 mM D,L-MTEH in 0.9% NaCl, 1 mM $MnCl_2$, pH 7.8) and incubated for 1 hour at 37° C. FIG. 6 shows the production of methionine (Met) and N-carbamoyl-methionine (C-Met) from D,L-MTEH for both catalysts. The whole cell catalyst with the improved hydantoinase from clone 22CG2 produced about 65 mM methionine within one hour whereas whole cell catalyst with the wild-type hydantoinase produced only 8 mM during the same reaction time. This demonstrates that an evolved hydantoinase without significant enantioselectivity but improved activity leads to a significant improvement for the production of methionine.

Having thus described exemplary embodiments of the present invention, it should be noted by those skilled in the art that the within disclosures are exemplary only and that various other alternatives, adaptations, and modifications may be made within the scope of the present invention. Accordingly, the present invention is not limited to the specific embodiments as illustrated herein, but is only limited by the following claims.

BIBLIOGRAPHY

1. Stinson, S. C. Counting on chiral drugs. *Chem. Eng. News* 76, 83–104.
2. Syldatk, C., Müeller, R., Siemann, M. and Wagner, F. Microbial and enzymatic production of D-amino aicds from DL-5-monosubstituted hydantoins. Hydrolysis and formation of hydantoins in Biocatalytic Production of Amino Acids and Derivatives (eds. Rozzell, J. D. and Wagner, F.) 75–127 (Hanser Publisher, New York, 1992).
3. Syldatk, C., Müller, R., Pietzsch, M. and Wagner, F. Microbial and enzymatic production of L-amino acids from DL-5-monosubstituted hydantoins. Hydrolysis and formation of hydantoins in Biocatalytic Production of Amino Acids and Derivatives (eds. Rozzell, J. D. and Wagner, F.) 131–1176 (Hanser Publisher, New York, 1992).
4. Drauz, K. (1997) Chiral amino acids: a versatile tool in the synthesis of pharmaceuticals and fine chemicals. *Chimia* 51, 310–314.
5. Wagner, F., Hantke, B., Wagner, T., Drauz & K., Bommarius, A. (1998) Microorganism, use thereof and process for production of L-.alpha.-amino acids. U.S. Pat. No. 5,714,355.
6. May, O., Siemann, M., Pietzsch, M., Kiess, M., Mattes, R. & Syldatk, C. (1998) Substrate-dependent enntioselectivity of a novel hydantoinase from Arthrobacter aurescens DSM 3745: purification and characterization as a new member of cyclic amidases. *J. Biotechno* 61, 1–13.
7. Wagner, T., Hantke, B. & Wagner, F. (1996) Production of L-methionine from D,L-5-(2-methylthioethyl) hdantoin by resting cells of a mutant strain of Arthrobacter species DSM 7330. *J. Biotechnol.* 46, 63–69.
8. Völkel, D. & Wagner, F. (1995) Reaction mechanism for the conversion of 5-monosubstituted hydantoins to enantiomerically pure L-amino acids. *Ann. NY Acad. Sci.* 750, 1–9.
9. Arnold, F. H. and Moore, J. C. (1997) Optimizing industrial enzymes by directed evolution. *Adv. Biochem. Eng. Biotech.* 58, 1–14.
10. Arnold, F. H. & Wintrode, P. L. Enzymes, directed evolution in Encyclopedia of Bioprocess Technology: Fermentation, Biocatalysis, and Bioseparation. (eds. Flickinger, M. C. & Drew, S. W.) 971–987 (John Wiley & Sons, Inc., New York, 1999).
11. Matcham, G. W. & Bowen, A. R. S. (1996) Biocatalysis for chiral intermediates: Meeting commercial and technical challenges. *CHIM. OGGI* 14, 20–24.
12. Reetz, M. T., Zonta, A., Schimossek, K., Liebeton, K. & Jaeger, K.-E. (1998) Creation of enantioselective biocatalysts for organic chemistry by in vitro evolution. *Angew. Chem. Int Ed.* 36, 2830–2832.
13. Reetz, M. T. & Jaeger, K.-E. (1999) Superior biocatalysts by directed evolution. *Top. Curr. Chem.* 200, 31–57.
14. Miyazaki, K. and Arnold, F. H. Exploring Nonnatural Evolutionary Pathways by Saturation Mutagenesis:

Rapid Improvement of Protein Function. *J. Molecular Evolution*, in press.
15. Handelsman, J., Rondon, M. R., Brady, S. F., Clardy, J. & Goodman, R. M. (1998) Molecular biological access to the chemistry of unknown soil microbes: A new frontier for natural products. *Chem. Biol.* 5, R245-R249.
16. Fersht, A. (ed.) in *Enzyme structure and mechanism*. p. 350 (W. H. Freeman and Company, New York, 1985).
17. Bailey, J. E. (1999) Lessons from metabolic engineering for functional genomics and drug discovery. *Nat. Biotechnol.* 17, 616–618.
18. Volff, J.-N., Eichenseer, C., Viell, P., Piendl, W. & Altenbuchner, J. (1996) Nucleotide sequence and role in DNA amplification of the direct repeats composing the amplificable element AUDI of *Streptomyces lividans*. 66 *MoL Microbiol.* 21, 1037–1047.
19. Rose, R. E. (1988) The nucleotide sequence of pACYC184. *Nucleic Acids Res.* 16, 355.
20. Yanisch-Perron, C., Viera, J. & Messing, J. (1984) Improved M13 phage cloning vectors and host strains: nucleotide sequences of the M13 mpl8 and pUC vectors. *Gene* 33, 103–109.
21. Luria. S. E., Adams, J. N. & Ting, R. C. (1960) Transduction of lactose-utilizing ability among strains of *Escherichia coli* and *Shigella dysenteriae* and properties of phage particles. *Virology* 12, 348–390.
22. Chen, C. S., Fujimoto, Y., Girdaukas, G. & Sih, C. J. (1982) Quantitative analysis of biochemical kinetic resolutions of enantiomers. *J. Am. Chem. Soc.* 104, 7294–7299.

What is claimed is:

1. A modified hydartoinase consisting of unmodified hydantoinase having SEQ. ID. NO. 2 which has been modified by an amino acid substitution at one or more amino acid positions selected from the group consisting of amino acid position numbers 95, 154, 180, 251 and 295.

2. A modified hydantoinase according to claim 1 wherein said one or more amino acid substitutions are selected from the group consisting of I95F, I95L, V154A, V180A, Q251R and V295A.

3. A modified hydantoinase according to claim 1 wherein said unmodified hydantoinase is modified by the amino acid substitutions I95F, V180A and Q251R as shown in SEQ ID NO: 14.

4. A modified hydantoinase according to claim 1 wherein said unmodified hydantoinase is modified by the amino acid substitutions I95L, V180A and Q251R as shown in SEQ ID NO: 12.

5. A modified hydantoinase according to claim 1 wherein said unmodified hydantoinase is modified by the amino acid substitutions I95L and Q251R as shown in SEQ ID NO: 6.

6. A modified hydantoinase according to claim 1 wherein said unmodified hydantoinase is modified by the amino acid sequence substitution V154A as shown in SEQ ID NO: 4.

7. A modified hydantoinase according to claim 1 wherein said unmodified hydantoinase is modified by the amino acid substitution V295A as shown in SEQ ID NO: 8.

8. A modified hydantoinase according to claim 1 wherein said unmodified hydantoinase is modified by the amino acid substitution I95L as shown in SEQ ID NO: 10.

9. A modified hydantoinase comprising an unmodified hydantoinase that has an amino acid sequence identity with SEQ. ID. NO. 2 which is about 97.5 percent and wherein said unmodified hydantoinase has been modified by an amino acid substitution at one or more amino acid positions selected from the group consisting of amino acid position numbers 95, 154, 251 and 295, and equivalent positions as determined by sequence alignment.

\* \* \* \* \*

UNITED STATES PATENT AND TRADEMARK OFFICE
CERTIFICATE OF CORRECTION

PATENT NO.    : 6,524,837 B1
DATED         : February 25, 2003
INVENTOR(S)   : Frances H. Arnold et al.

Page 1 of 1

It is certified that error appears in the above-identified patent and that said Letters Patent is hereby corrected as shown below:

<u>Title page,</u>
Item [73], please replace the Assignees with the following:

-- [73]  Assignee:  California Institute of Technology, Pasadena, CA (US);
                    Degussa-Hüls Aktiengesellschaft Frankfurt am Main (DE) --

Signed and Sealed this

Ninth Day of September, 2003

JAMES E. ROGAN
*Director of the United States Patent and Trademark Office*